United States Patent

Bremen et al.

[11] 4,271,293
[45] Jun. 2, 1981

[54] BENZOFURANYL-BENZIMIDAZOLES

[75] Inventors: Josef Bremen, Leverkusen; Bernhard Wehling, Cologne; Carl-Wolfgang Schellhammer, Bergisch-Gladbach, all of Fed. Rep. of Germany

[73] Assignee: Bayer Aktiengesellschaft, Leverkusen, Fed. Rep. of Germany

[21] Appl. No.: 38,309

[22] Filed: May 11, 1979

[30] Foreign Application Priority Data

May 13, 1978 [DE] Fed. Rep. of Germany ....... 2821116

[51] Int. Cl.³ .......................................... C07D 405/14
[52] U.S. Cl. .............................. 542/435; 252/301.29; 548/255; 548/256; 548/260; 548/243; 548/259; 260/346.22; 260/152
[58] Field of Search ............... 548/255, 259, 260, 256; 542/435

[56] References Cited
FOREIGN PATENT DOCUMENTS 2522139 12/1975 Fed. Rep. of Germany ........... 548/255

Primary Examiner—Donald G. Daus
Assistant Examiner—James H. Turnipseed
Attorney, Agent, or Firm—Sprung, Felfe, Horn, Lynch & Kramer

[57] ABSTRACT

Compounds of the formula

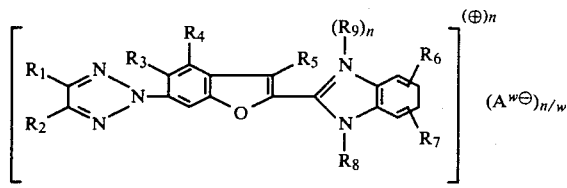

in which
  $R_1$ denotes aryl, alkyl, aralkyl, styryl or alkoxy,
  $R_2$ denotes hydrogen, cyano, carboxyl or alkoxycarbonyl, inter alia,
  $R_3$, $R_4$, $R_6$ and $R_7$ denote hydrogen, alkyl, alkoxy or halogen,
  $R_5$ denotes hydrogen, alkyl or aryl,
  $R_8$ and $R_9$ denote hydrogen, cycloalkyl, alkenyl, alkyl or aralkyl,
  $A^\ominus$ denotes an anion,
  w denotes the valency of the anion A and
  n denotes 0 or 1, are outstandingly suitable for optically brightening synthetic fibre materials, in particular acrylic fibres.

The new brighteners are prepared and used in accordance with methods which are in themselves known.

3 Claims, No Drawings

BENZOFURANYL-BENZIMIDAZOLES

The present invention relates to new benzofuranyl-benzimidazoles, intermediate products for their preparation, a process for their preparation and their use for optically brightening organic materials.

The new benzofuranyl-benzimidazoles correspond to the formula

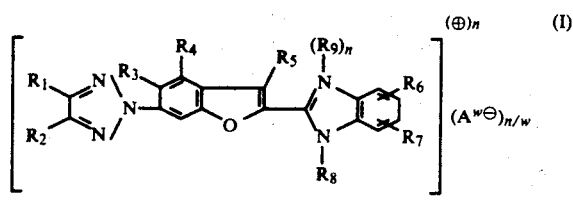

in which
- $R_1$ denotes aryl, alkyl, aralkyl, styryl or alkoxy, which can be substituted,
- $R_2$ denotes hydrogen, cyano, carboxy, a —COOR radical, R being the radical of an alcohol, or optionally substituted carbamoyl, or acylamino, or is the same as $R_1$, or
- $R_1$ and $R_2$ together denote a fused-on hydro-aromatic or aromatic ring, which can be substituted,
- $R_3$ and $R_4$ denote hydrogen, optionally substituted alkyl, optionally substituted alkoxy or halogen,
- $R_5$ denotes hydrogen, an optionally substituted alkyl group or an optionally substituted aryl radical,
- $R_6$ denotes hydrogen, an optionally substituted alkyl or optionally substituted alkoxy group, halogen, an optionally substituted aryl radical, an optionally substituted alkylsulphonyl or an optionally substituted phenylsulphonyl radical, a sulpho or carboxyl group or a functional derivative thereof, including the cyano group, or the trifluoromethyl group,
- $R_7$ denotes a hydrogen or halogen atom or an optionally substituted alkyl or optionally substituted alkoxy group,
- $R_8$ denotes a cycloalkyl, alkenyl, alkyl, aryl or aralkyl group, it being possible for the hydrocarbon radicals mentioned to be substituted, or, in the case where n=0, also a hydrogen atom,
- $R_9$ denotes a hydrogen atom or a cycloalkyl, alkenyl, alkyl or aralkyl group, it being possible for the hydrocarbon radicals mentioned to be substituted,
- $A^\ominus$ denotes a colourless anion of an inorganic or organic acid,
- w denotes the valency of the anion A and
- n represents 0 or 1.

Particularly suitable alkyl groups $R_1$, $R_3$, $R_4$, $R_5$, $R_6$, $R_7$, $R_8$ and $R_9$ are those with 1-12 C atoms, which can be substituted by halogen, hydroxyl, alkoxy with 1-4 C atoms or cyano. Suitable aryl groups $R_1$, $R_5$, $R_6$ and $R_8$ are, in particular, phenyl and naphthyl, which can be substituted by halogen, cyano, alkoxy with 1-4 C atoms, alkyl with 1-4 C atoms, carboxyl or phenyl. Suitable aralkyl radicals $R_1$, $R_6$, $R_8$ and $R_9$ are, in particular, phenyl-alkyl radicals with 1-4 C atoms in the alkylene chain. Suitable alkoxy groups $R_1$, $R_3$, $R_4$, $R_6$ and $R_7$ are those with 1-10 C atoms, which can be substituted by hydroxyl, halogen or cyano.

$R_2$ in the meaning of —COOR represents, in particular, ($C_1$-$C_4$-alkoxy)-carbonyl radicals; $R_2$ in the meaning of optionally substituted carbamoyl represents, in particular, $H_2NCO$—, $R'NH$—CO— and $(R')_2NCO$—, R' designating a $C_1$-$C_4$-alkyl radical, which is preferably substituted by —OH or —CN.

Particularly suitable acylamino groups $R_2$ are formylamino, alkylcarbonylamino with 1-4 C atoms in the alkyl radical, alkoxycarbonylamino with 1-4 C atoms in the alkoxy radical, alkylsulphonylamino with 1-4 C atoms in the alkyl radical, or benzoylamino, which can be substituted in the benzene ring by $C_1$-$C_4$-alkyl, $C_1$-$C_4$-alkoxy, halogen, carboxyl or cyano.

The fused-on aromatic ring formed by $R_1$ and $R_2$ can be a benzene or naphthalene ring, both of which can be optionally substituted by non-chromophoric groups.

By "halogen", as the meaning of $R_3$, $R_4$, $R_6$ and $R_7$, there are to be understood fluorine, chlorine and bromine, in particular chlorine and bromine and preferably chlorine.

Examples which may be mentioned of functional derivatives of the sulpho or carboxyl group (meaning of $R_6$) are esters, amides and salts, sulphonic acid esters which are particularly preferred being the aromatic esters. The cyano group may also be mentioned as a derivative of the carboxyl group.

The alkylsulphonyl radicals $R_6$ preferably contain 1 to 6 C atoms and can be substituted, in particular by halogen, such as Cl and Br, hydroxyl, alkoxy with 1 to 4 C atoms or cyano.

The phenylsulphonyl radicals $R_6$ are either unsubstituted or carry, preferably, halogen, such as Cl and Br, cyano, $C_1$-$C_4$-alkoxy, $C_1$-$C_4$-alkyl, carboxyl or phenyl as substituents.

The anion $A^\ominus$ can be any colourless anion of an organic or inorganic acid. Its nature has no substantial influence on the brightening properties of the compounds according to the invention. The anion is as a rule introduced by the preparation process (quaternisation or protonation), but it can also be replaced by another by known methods (see, for example, Houben-Weyl, Methoden der organischen Chemie (Methods of Organic Chemistry), volume XI/2, pages 620–626). Halogen anions can be replaced by anions of aliphatic carboxylic acids in accordance with the method of DOS (German Published Specification) 2,549,436, by reacting the halide in the presence of these carboxylic acids, using epoxides as hydrogen halide acceptors.

In the case of compounds of the formula (I) which contain a —$SO_3H$ radical, the strongly acid sulpho group can form an inner salt with the basic imidazole ring. The group $SO_3^\ominus$ as one of the substituents of the benzimidazole ring can thus also function as the anion $A^\ominus$ in quaternised or protonated compounds of the formula (I).

Within the scope of the benzofuranyl-benzimidazoles of the formula (I), the compounds of the formula

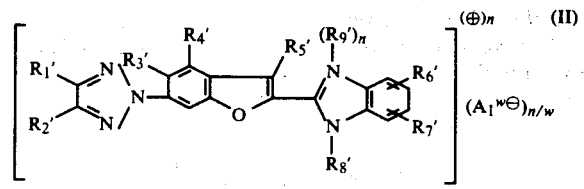

in which
- $R_1'$ denotes an alkyl group with 1 to 12 carbon atoms, an alkoxy group with 1-4 carbon atoms, a phenyl radical, which can optionally be substituted by alkyl with 1–4 C atoms, phenyl, alkoxy with 1–4 C atoms or chlorine, a benzyl radical or a styryl radical, $R_2'$ denotes hydrogen, cyano, carboxyl, $C_1$–$C_4$-alkylcarbonylamino, benzoylamino or the radical $R_1'$, or $R_1'$ and $R_2'$ together denote a fused-on naphthalene ring or benzene ring, which can optionally be substituted by alkyl with 1 to 4 carbon atoms and/or alkoxy with 1 to 4 carbon atoms, $R_3'$ and $R_4'$ independently of one another denote hydrogen, methyl, ethyl, methoxy or chlorine, $R_5'$ denotes hydrogen, alkyl with 1 to 4 carbon atoms, preferably methyl, or phenyl which is optionally substituted by methyl and/or methoxy, $R_6'$ denotes hydrogen, alkyl with 1 to 4 carbon atoms, preferably methyl, methoxy, chlorine, alkylsulphonyl with 1 to 4 carbon atoms, cyano or a sulpho or carboxyl group or a functional derivative thereof, $R_7'$ denotes hydrogen, methyl, methoxy or Cl, $R_8'$ denotes alkyl with 1 to 4 carbon atoms, preferably methyl, hydroxyalkyl with 2 to 4 carbon atoms, cyanoethyl or phenyl, cyclohexyl or benzyl, optionally substituted by chlorine, methyl or methoxy, $R_9'$ denotes alkyl with 1 to 4 carbon atoms, optionally substituted by hydroxyl or alkoxy with 1 to 4 carbon atoms, benzyl which is optionally substituted by chlorine or methoxy or a radical —CH$_2$CN, —CH$_2$CONH$_2$ or —CH$_2$COOR, wherein R an alkyl group with 1 to 4 carbon atoms, preferably methyl, n denotes the number 0 or 1, $A_1^\ominus$ denotes a halide, formate, acetate, lactate, CH$_3$SO$_4^\ominus$, C$_2$H$_5$SO$_4^\ominus$, C$_6$H$_5$SO$_3^\ominus$, p—CH$_3$—C$_6$H$_4$SO$_3^\ominus$, p—Cl—C$_6$H$_4$SO$_3^\ominus$, carbonate or bicarbonate and . w denotes the valency of the anion $A_1$ are to be singled out.

Furthermore, compounds of the formula

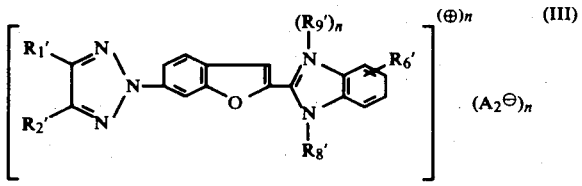

wherein $R_1'$, $R_2'$, $R_6'$, $R_8'$ and $R_9'$ have the meaning indicated above, n denotes the number 0 or 1 and $A_2^\ominus$ denotes a halogen ion, methylsulphate ion, ethylsulphate ion or p-tolylsulphate ion, are of particular interest.

The invention furthermore relates to compounds of the formula

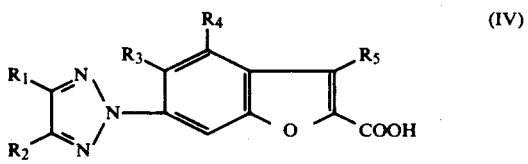

in which $R_1$ denotes aryl, alkyl, aralkyl, styryl or alkoxy, which can be substituted, $R_2$ denotes hydrogen, cyano, carboxyl, a —COOR radical, R being the radical of an alcohol, or optionally substituted carbamoyl, or acylamino, or is the same as $R_1$, or $R_1$ and $R_2$ together denote a fused-on hydro-aromatic or aromatic ring, which can be substituted, $R_3$ and $R_4$ denote hydrogen, optionally substituted alkyl, optionally substituted alkoxy or halogen and $R_5$ denotes hydrogen, an optionally substituted alkyl group or an optionally substituted aryl radical.

These compounds are intermediate products for the preparation of the benzofuranyl-benzimidazoles of the formula (I).

Particularly suitable alkyl groups $R_1$, $R_3$, $R_4$ and $R_5$ are those with 1–12 C atoms, which can be substituted by halogen, hydroxyl, alkoxy with 1–4 C atoms or cyano. Suitable aryl groups $R_1$ and $R_5$ are, in particular, phenyl and naphthyl, which can be substituted by halogen, cyano, alkoxy with 1–4 C atoms, alkyl with 1–4 C atoms, carboxyl or phenyl. Suitable aralkyl radicals $R_1$ are, in particular, phenyl-alkyl radicals with 1–4 C atoms in the alkylene chain. Suitable alkoxy groups $R_1$, $R_3$ and $R_4$ are those with 1–10 C atoms, which can be substituted by hydroxyl, halogen or cyano.

$R_2$ in the meaning of —COOR represents, in particular, (C$_1$–C$_4$-alkoxy)-carbonyl radicals; $R_2$ in the meaning of optionally substituted carbamoyl represents, in particular, H$_2$NCO—, R'NH—CO— and (R')$_2$NCO—, R' designating a C$_1$–C$_4$-alkykl radical, which is preferably substituted by —OH or —CN.

Particularly suitable acylamino groups $R_2$ are formylamino, alkylcarbonylamino with 1–4 C atoms in the alkyl radical, alkoxycarbonylamino with 1–4 C atoms in the alkoxy radical, alkylsulphonylamino with 1–4 C atoms in the alkyl radical, or benzoylamino, which can be substituted in the benzene ring by C$_1$–C$_4$-alkyl, C$_1$–C$_4$-alkoxy, halogen, carboxyl or cyano.

The fused-on aromatic ring formed by $R_1$ and $R_2$ can be a benzene ring or naphthalene ring, both of which can be optionally substituted by non-chromophoric groups.

By "halogen", as the meaning of $R_3$ and $R_4$, there are to be understood fluorine, chlorine and bromine, in particular chlorine and bromine and preferably chlorine.

Within the scope of this invention, the compounds of the formula (IVa)

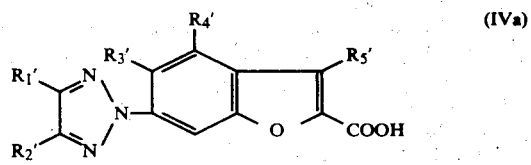

in which $R_1'$ denotes an alkyl group with 1 to 12 carbon atoms, an alkoxy group with 1 to 4 carbon atoms, a phenyl radical, which can optionally be substituted by alkyl with 1–4 C atoms, phenyl, alkoxy with 1–4 C atoms or chlorine, a benzyl radical or a styryl radical, $R_2'$ denotes hydrogen, cyano, carboxyl, C$_1$–C$_4$-alkylcarbonylamino, benzoylamino or the radical $R_1'$, or $R_1'$ and $R_2'$ together denote a fused-on naphthalene ring or benzene ring, which can optionally be substituted by alkyl with 1 to 4 carbon atoms or alkoxy with 1 to 4 carbon atoms, $R_3'$ and $R_4'$ independently of one another denote hydrogen, methyl, ethyl, methoxy or chlorine and $R_5'$ denotes hydrogen, methyl with 1 to 4 carbon atoms, preferably methyl, or phenyl which is optionally substituted by methyl and/or methoxy, are to be singled out.

To prepare the compounds of the formula (I) using the carboxylic acids (IV), a compound of the formula

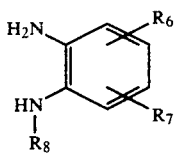
(V)

in which $R_6$, $R_7$ and $R_8$ have the meaning indicated above, is acylated with a compound of the formula (IV) or one of its functional derivatives, with regard to the carboxyl group, and the imidazole cyclisation is brought about, preferably in the presence of acid condensing agents, such as, for example, acetic acid, hydrogen chloride, boric acid, zinc chloride, polyphosphoric acid, phosphoric acid or p-toluenesulphonic acids, in a manner which is in itself known. The resulting compounds are optionally quaternised or protonated with an acid in a known manner.

Compounds of the formula (I) wherein n represents zero (non-quaternised compounds) are also obtained by a process in which compounds of the formula (I) which are unsubstituted on the imidazole ring and wherein $R_8$ denotes hydrogen and n denotes zero are reacted with alkylating agents in the presence of compounds which have a basic action by known processes.

By functional derivatives of the carboxylic acids of the formula (IV) there are to be understood salts, halides, esters, amides, imino-ethers and nitriles thereof.

The preparation of the acid addition products (compounds of the formula (I) in which $R_9=H$ and $n=1$) or of the quaternary ammonium salts, that is to say the reaction of compounds of the formula (I) wherein n is the number 0 with a protonating agent or quaternising agent of the formula $R_9$—A wherein $R_9$ has the meaing indicated above and A denotes the radical which is converted into the anion $A^\ominus$ during the quaternisation or protonation, can be carried out in the customary manner, preferably in a solvent, it being appropriate to employ at least one molar equivalent of the protonating agent or quaternising agent.

If the preparation of compounds of the formula (I) which are quaternised with alkyl radicals is desired, the alkylating agents used are preferably dialkyl sulphates, such as dimethyl sulphate and diethyl sulphate, alkyl halides, such as methyl chloride, ethyl iodide or bromide, propyl iodide or bromide and butyl iodide or bromide, allyl chloride or bromide, crotyl chloride or bromide and alkylbenzenesulphonates, such as p-methylbenzenesulphonate, ethylbenzenesulphonate or chlorobenzenesulphonate. If the preparation of compounds of the formula (I) which are quaternised with a benzyl radical is desired, benzyl halides, such as benzyl chloride, are preferably used for the benzylation. Examples of other quaternising agents are $BrCH_2CH_2OH$, $BrCH_2CHOHCH_3$, halogenoacetic acid derivatives, such as $ClCH_2CO_2CH_2CH_3$, $BrCH_2COOH$, $BrCH_2COOCH_3$, $ClCH_2CN$, $ClCH_2CONH_2$, $ClCH_2CONHCH_3$ and $ClCH_2CON(CH_3)_2$, and ethylene oxide or propylene oxide in the presence of suitable anions, such as, for example, anions of formic acid, acetic acid or lactic acid.

If protonated compounds of the formula (I) are desired, that is to say acid addition salts of these compounds ($R_9=H$, $n=1$), the protonating agents used are, in particular, mineral acids. In principle, all strong to medium-strength organic acids or mineral acids are suitable, it being possible for the anions to be replaced by double decomposition. For example, the desired acid is added dropwise to a solution of the benzimidazole, whilst stirring, whereupon the salt precipitates. Gaseous acid, for example hydrochloric acid, are passed in.

Suitable solvents in which the protonation or quaternisation can be carried out are, in general, all the inert solvents. Those which dissolve the starting material and from which the end product separates out immediately are preferred. Examples which may be mentioned are: aromatic hydrocarbons, such as benzene, toluene and xylene; halogenated hydrocarbons, such as trichloroethane, tetrachloroethylene, chlorobenzene or dichlorobenzene, and furthermore also nitrobenzene, alkanols and open-chain or cyclic ethers, such as butanol, dibutyl ether, ethylene glycol monomethyl ether, ethylene glycol monoethyl ether, anisole or dioxane; ketones, such as cyclohexanone or methyl ethyl ketone; fatty acid amides, such as dimethylformamide or dimethylacetamide; sulphoxides, such as dimethylsulphoxide, and carboxylic acid esters, such as ethyl acetate or butyl acetate. The reaction is carried out, for example, at temperatures of 60° to 180° C., preferably 90° to 140° C. It is sometimes also advantageous to use excess alkylating agent as the solvent.

Alternatively, the compounds of the formula (I) can also be prepared by a process in which an o-nitroaniline of the formula

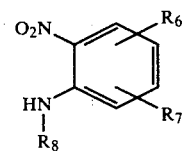
(VI)

wherein $R_6$, $R_7$ and $R_8$ have the meaning indicated under formula (I), is acylated with a compound of the formula (IV) or a functional derivative thereof, the nitro group is reduced in an acid medium, for example with stannous chloride/hydrochloric acid, and cyclisation to form the imidazole ring is simultaneously brought about.

The starting materials of the formula (V) are prepared in a manner which is in itself known be reacting o-chloro-nitrobenzene derivatives with primary amines or ammonia to give the correspondingly substituted o-nitroanilines and reducing the latter, for example by means of catalytic hydrogenation (compare Belgian Patent Specification No. 595,327, DE-OS (German Published Specification) No. 2,239,614 and DE-OS (German Published Specification) No. 1,522,412). It is better to reduce o-nitroanilines having substituents which can easily be hydrogenated catalytically, such as, for example, allyl groups, with sodium bisulphite or iron (Bechamp method).

The starting compounds of the formula (IV) can be prepared:

(1) by rearrangement of coumarilic acid (compare Krauch-Kunz, Reaktionen der organischen Chmie (Reactions of Organic Chemistry), 3rd edition, page 449) from the coumarin derivatives of the formula

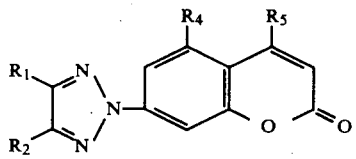

(VII)

wherein $R_1$, $R_2$, $R_3$, $R_4$ and $R_5$ have the meaning indicated in formula IV, or (2) by reaction of compounds of the formula

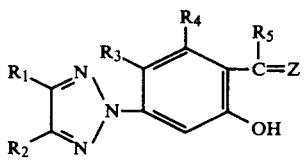

(VIII)

wherein $R_1$, $R_2$, $R_3$, $R_4$ and $R_5$ have the meaning indicated in formula (IV) and Z is O or N—R", wherein R" denotes an optionally substituted phenyl radical, with halogenomalonic esters of the formula

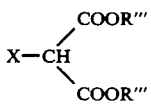

(IX)

wherein

X denotes chlorine, bromine or iodine, or particular bromine, and

R''' denotes an alkyl group, in particular methyl or ethyl, in a manner which is in itself known [compare S. Tanaka, J. Am. Chem. Soc. 73, page 872 (1951)], the compound of the formula

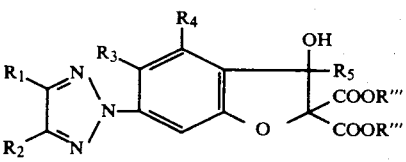

(X)

wherein $R_1$, $R_2$, $R_3$, $R_4$ and $R_5$ have the meaning indicated in formula (IV), first being formed, and then being converted into the compound of the formula (IV) by saponification, dehydration and decarboxylation; in this procedure, the first reaction stage is appropriately carried out in polar solvents, such as alcohol, such as, for example, methanol, ethanol or ethylene glycol monomethyl ether, ketones, such as acetone, methyl ethyl ketone or methyl isobutyl ketone, fatty acid amides, such as dimethylformamide of dimethylacetamide; or sulphoxides, such as dimethylsulphoxide, in the presence of acid-binding substances, such as sodium hydroxide, potassium hydroxide, sodium carbonate, potassium carbonate, sodium acetate, sodium methylate or tertiary organic amines, such as triethylamine or pyridine, at temperatures from 50° to 120° C., and the second reaction stage is appropriately carried out in a polar solvent, in particular an alcohol, such as, for example, methanol, ethanol, propanol and ethylene glycol monomethyl ether, in the presence of a strong base, such as sodium hydroxide or potassium hydroxide, or an aqueous solution of a strong base, at temperatures from 60° C. to 150° C., or (3) by reaction of the compounds of the formula (VIII) with halogenoacetic acid esters of the formula

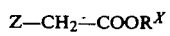

$$Z-CH_2-COOR^x$$ (XI)

wherein

Z denotes chlorine, bromine or iodine, in particular chlorine or bromine, and $R^x$ denotes an alkyl group, in a manner which is in itself known (compare Bull. Soc. Chim. France 1971, page 4,329 to 4,331), the reaction appropriately being carried out in solution in the presence of acid-binding substances, such as sodium hydroxide, potassium hydroxide, sodium carbonate, potassium carbonate, sodium bicarbonate, sodium acetate, potassium acetate, sodium methylate, triethylamine or pyridine. Examples of suitable solvents are water, alcohols, such as methanol, ethanol or ethylene glycol monomethyl ether, ketones, such as acetone, methyl ethyl ketone or metyl isobutyl ketone, carboxylic acid derivatives, such as acetonitrile or dimethylformamide, or n-methylpyrrolidone. Mixtures of the solvents mentioned are also suitable.

(4) Furthermore, the compounds of the formula (IV) can also be prepared by cyclisation of oximinohydrazones of the formula

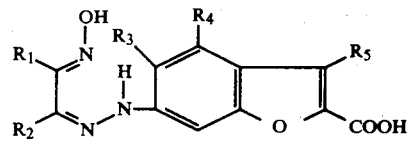

(XII)

wherein $R_1$, $R_2$, $R_3$, $R_4$ and $R_5$ have the meaning indicated under formula (IV), by known processes (compare German Offenlegungsschrift (German Published Specification) No. 1,670,914 and British Patent Specification No. 1,154,995).

The oximinohydrazones of the formula (II) are prepared, for example, from 6-nitrobenzofuranecarboxylic acid derivatives of the formula

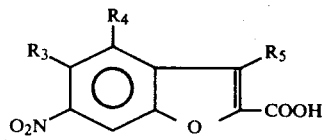

(XIII)

wherein $R_3$, $R_4$ and $R_5$ have the meaning indicated under formula (IV), by reduction of the nitro group, diazotisation of the resulting amino group, reduction of the diazonium group to give the hydrazino group and reaction of the product with α-oximinoketones of the formula

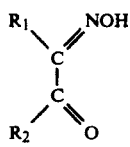 (XIV)

wherein $R_1$ and $R_2$ have the meaning indicated under formula (IV).

(5) A further possibility for the preparation of the compounds of the formula (IV) is decarboxylation and rearrangement, under the influence of heat, of the azo dyestuffs of the formula

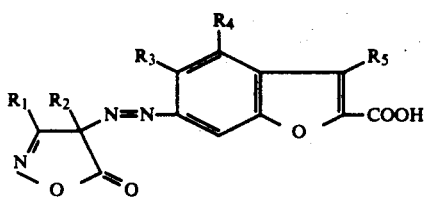 (XV)

wherein $R_1$, $R_2$, $R_3$, $R_4$ and $R_5$ have the meaning indicated under formula (IV), which are formed when the diazonium salts of the formula

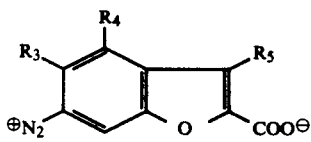 (XVI)

wherein $R_3$, $R_4$ and $R_5$ have the meaning indicated under formula (IV), are coupled to isoxazolin-5-ones, substituted in the 3-position and 4-position, of the formula

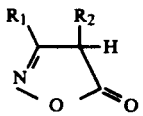 (XVII)

wherein $R_1$ and $R_2$ have the meaning indicated under formula (IV).

(6) Finally, the compounds of the formula (IV) in which $R_1$ and $R_2$ together denote a fused-on aromatic ring can be prepared by coupling the diazonium salt of the formula (XVI) to a primary aromatic amine of the benzene series or naphthalene series to give an o-aminoazo compound of the formula

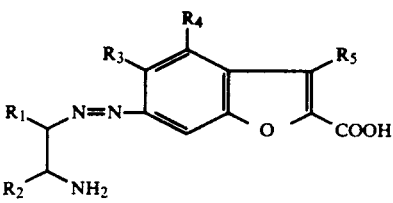 (XVIII)

wherein
$R_1$ and $R_2$ denote a fused-on aromatic ring system and $R_3$, $R_4$ and $R_5$ have the meaning indicated in the case of formula (IV),
and subsequent oxidation of the product to the triazole ring system by known methods (compare German Offenlegungsschrift (German Published Specification) No. 1,519,471).

The compounds of the formula (I) according to the invention exhibit a pronounced fluorescence in the dissolved or finely disperse state. They are suitable for optically brightening the most diverse synthetic, semi-synthetic or natural organic high-molecular materials, above all for optically brightening fibers, filaments, woven fabrics or films of a synthetic origin, for example of polyesters, such as polyterephthalic acid glycol esters, polyamides, such as polymers based on hexamethylenediamine adipate or caprolactam, cellulose esters, such as cellulose 2½-acetate and cellulose triacetate, and in particular of polyacrylonitrile.

Colourless, high-molecular organic material in the form of fibres is preferably brightened. An aqueous solution or dispersion of benzofuranyl-benzimidazoles of the formula (I) according to the invention is advantageously used for brightening these fibre materials.

In this case, the brightener dispersion or solution preferably contains from 0.005 to 0.5% of compounds according to the invention, relative to the fibre material. In addition, the dispersion can contain auxiliaries, such as dispersing agents, for example condensation products of fatty alcohols or alkylphenols containing 10 to 18 carbon atoms with 15 to 25 mols of ethylene oxide, or condensation products of alkylmonoamines or polyamines containing 16 to 18 carbon atoms with at least 10 mols of ethylene oxide, organic acids, such as formic acid, oxalic acid or acetic acid, washing agents, swelling agents, such as dichlorobenzenes or trichlorobenzenes, wetting agents, such as sulphosuccinic acid alkyl esters, bleaching agents, such as sodium chlorite, peroxides or hydrosulphites, and if desired other classes of brighteners, such as, for example, stilbene derivatives which have an affinity for cellulose.

The fibre material is brightened with the aqueous brightener liquor either by the exhaustion process, preferably at temperatures from 30° to 150° C., or by the padding process. In the latter case, the goods are impregnated with, for example, a 0.2 to 0.5% strength brightener dispersion and the dyed material is finished, for example by dry or moist heat treatment, for example by steaming under two atmospheres or, after drying has been carried out, by heating to 180° to 220° C. under dry conditions for a short time, if appropriate the fabric being simultaneously heat set. Finally, the fibre material treated in this manner is rinsed and dried.

Colourless, high-molecular, organic material optically brightened according to the invention, especially natural or synthetic fibre material brightened by the exhaustion process, has a pleasant, pure white appearance and exhibits a blue-violet to bluish-tinged fluorescence; material of this type dyed in light colour shades and whitened according to the invention is distinguished by a pure colour shade.

Wash liquors which contain benzofuranes of the formula (I) impart during washing a brilliant aspect in daylight to the textile fibres treated therewith, for example synthetic polyamide fibres, polyester fibres and cellulose ester fibres, but in particular polyacrylonitrile fibres. The brightenings achieved have a good fastness and are particularly fast to light and resistant to washing.

The new optical brighteners according to the present invention can, for example, also be employed in the following use forms:

(a) mixed with dyestuffs (shading) or pigments (coloured pigments or especially, for example, white pigments), or as an additive to dyebaths, printing pastes, discharge pastes or reserve pastes, and furthermore also for the after-treatment of dyeings, prints or discharge prints.

(b) mixed with so-called "carriers", wetting agents, plasticisers, swelling agents, antioxidants, light stabilisers, heat stabilisers and chemical bleaching agents (chlorite bleach or bleaching bath additives), (c) mixed with crosslinking agents or finishing agents (for example starch or synthetic finishes), and in combination with the most diverse textile finishing processes, in particular synthetic resin finishes (for example creaseproof finishes, such as "wash-and-wear", "permanent-press" or "no-iron"), as well as flameproof finishes, soft handle finishes, antisoiling finishes or antistatic finishes, or antimicrobial finishes, (d) incorporation of the optical brighteners into polymeric carriers (polymerisation products, polycondensation products or polyaddition products), in a dissolved or dispersed form, for use, for example, in coating agents, impregnating agents or binders (solutions, dispersions and emulsions) for textiles, fleeces, paper and leather, (e) as additives to so-called "master batches", (f) as additives to the most diverse industrial products, in order to render these more marketable (for example improving the aspect of soaps, washing agents and pigments, (g) in combination with other substances having an optically brightening action, (h) in spinning bath preparations, that is to say as additives to spinning baths, such as are used for improving the slip for the further processing of synthetic fibres, or from a special bath before stretching the fibre, (i) as scintillators for various purposes of a photographic nature, such as, for example, for electrophotograhic reproduction or supersensitisation, and (j) depending on the substituents, as laser dyestuffs.

EXAMPLE 1

7.0 g of 6-(naphth-[1,2-d]1,2,3-triazol-2-yl)-benzofurane-2-carboxylic acid chloride are introduced into a solution of 2.7 g of N-methyl-o-phenylenediamine in 60 ml of pyridine at room temperature in the course of 5 minutes. The mixture is subsequently stirred for 15 minutes and is then stirred at 80°–85° C. for 6 hours. During thisperiod, 6-(naphth-[1,2-d]1,2,3-triazol-2-yl)-benzofurane-2-carboxylic acid N-methyl-o-aminoanilide precipitates in the form of yellowish white crystals. After cooling the mixture to 5° C., the crystals are filtered off and rinsed with a little pyridine. The residue on the filter is suspended in 200 ml of water and the suspension is adjusted to pH 2–3 with 10% strength hydrochloric acid. Thereafter, the solid is filtered off and washed several times with water.

The acylation product obtained above is suspended, whilst still moist, in 150 ml of glycol monomethyl ether at 80° C. 10 ml of cconcentrated hydrochloric acid are added, whereupon the product dissolves immediately. The solution is stirred under reflux for 1½ hours. During this period, the benzimidazole of the formula

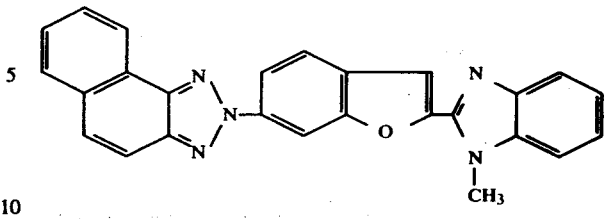

gradually crystallises out as the hydrochloride. The mixture is cooled to 5° C. and the crystals are filtered off. For conversion into the free base, the resulting product is suspended in 150 ml of methanol, and 5 ml of triethylamine are added at 50° C. The mixture is stirred at this temperature for one hour and the solid is filtered off, washed with methanol and dried. Recrystallisation from dimethylformamide gives 6.1 g (73% of theory) of the compound of the formula (101) in the form of yellowish crystals which exhibit a blue-violet fluorescence in solution.

The 6-(naphth[1,2-d]-1,2,3-triazol-2-yl)-benzofurane-2-carboxylic acid chloride used as the starting material is prepared as follows:

A suspension of 28.9 g of 4-(naphth-[1,2-d]-1,2,3-triazol-2-yl)-salicyl-aldehyde, 31.1 g of bromomalonic acid diethyl ester and 20.7 g of potassium carbonate in 400 ml of dimethylsulphoxide is stirred at 80° C. for 2 hours. Thereafter, the solvent is distilled off in vacuo, the residue is stirred with 400 ml of ethanol, the mixture is acidified with 20% strength sulphuric acid and the solid is filtered off and washed with water. The filter-cake is boiled for 6 hours in 500 ml of ethanol which contains 22.4 g of 50% strength potassiumm hydroxide solution. Thereafter, the solvent is distilled off in vacuo and the residue is stirred with 500 ml of water. The mixture is rendered acid to Congo red with concentrated hydrochloric acid and the solid is filtered off. After recrystallisation from ethylene glycol monomethyl ether with the aid of Tonsil, 21.1 g (64% of theory) of 6-(naphth[1,2-d]-1,2,3-triazol-2-yl)-benzofurane-2-carboxylic acid with a melting point of >300° C. are obtained.

8.0 g of the benzofurane-2-carboxylic acid thus prepared are heated under reflux in 10 g of thionyl chloride, 250 ml of toluene and 0.5 ml of dimethylformamide for 2 hours. Thereafter, the mixture is cooled to 0° C. and the solid is filtered off, recrystallised from toluene and dried. 7.7 g (91% of theory) of 6-(naphth-[1,2-d]-1,2,3-triazol-2-yl)-benzofurane-2-carboxylic acid chloride are obtained in the form of yellowish crystals which melt at 230°–231° C.

EXAMPLE 2

3.0 g of the compound of the formula (101) are dissolved in 150 ml of 1,2-dichlorobenzene by warming to 140° C. 2.0 ml of dimethyl sulphate are added dropwise to the resulting solution at 120° C. When the dropwise addition has ended, the mixture is stirred at 130°–140° C. for 3 hours. During this period, the quaternary benzimidazole gradually precipitates. The mixture is cooled to 90°–100° C. and the precipitate is filtered off, rinsed several times with hot 1,2-dichlorobenzene and dried at 100° C. under an oil pump vacuum. 3.8 g (97% of theory) of the quaternary benzofuranyl-benzimidazole of the formula

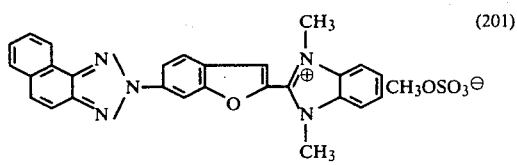

are obtained in the form of yellow crystals.

The compound dissolves in water giving a solution with a blue fluorescence in daylight and is outstandingly suitable for brightening polyacrylonitrile fibres.

EXAMPLE 3

6.8 g of 6-(4-methyl-5-phenyl-1,2,3-triazol-2-yl)-benzofurane-2-carboxylic acid chloride are introduced into a solution of 2.7 g of N-methyl-o-phenylenediamine in 60 ml of pyridine at room temperature in the course of 5 minutes. During this period, the temperature rises to 35°–40° C. The mixture is subsequently stirred for 15 minutes, and then stirred at 80°–85° C. for 6 hours. It is cooled to room temperature and poured into 600 ml of water. 30 ml of concentrated hydrochloric acid are added, and the mixture is stirred at room temperature for 30 minutes. A crystalline precipitate is obtained. The precipitate is filtered off and washed several times with 5% strength hydrochloric acid, and the still moist intermediate product is cyclised in ethylene glycol monomethyl ether, as described in Example 1 for the preparation of the benzimidazole of the formula (101). 5.2 g (64% of theory) of the benzimidazole of the formula

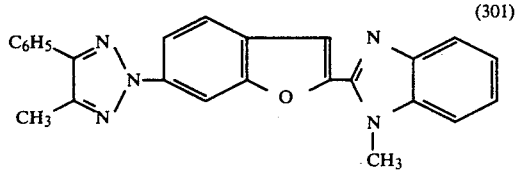

are obtained in the form of yellowish crystals which exhibit a blue-violet fluorescence in solution.

If, instead of N-methyl-o-phenylenediamine, equivalent amounts of 2-methylamino-5-methylsulphonyl-aniline or 2-methylamino-5-methyl-aniline or 2-methylamino-5-chloroaniline are used and the procedure is otherwise as described above, the benzimidazoles of the following formula are obtained

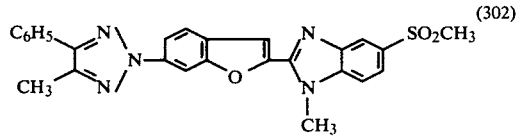

Colour of fluorescence in solution: neutral blue or

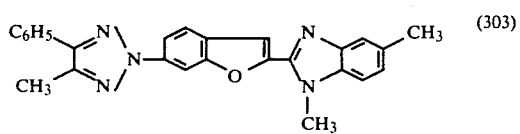

Colour of fluorescence in solution: blue-violet or

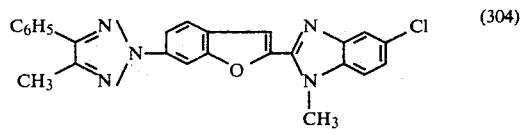

Colour of fluorescence in solution: neutral blue

The 6-(4-methyl-5-phenyl-1,2,3-triazol-2-yl)-benzofurane-2-carboxylic acid chloride used as the starting material is obtained by a preparation analogous to the preparation, described in Example 1, of 6-(naphth[1,2-d]-1,2,3-triazol-1-yl)-benzofurane-2-carboxylic acid chloride when 4-(naphth[1,2-d]-1,2,3-triazol-2-yl)-salicylaldehyde is replaced by the equivalent amount of 4-(4-methyl-5-phenyl-1,2,3-triazol-2-yl)-salicylaldehyde and the procedure followed is otherwise as described in Example 1.

The 6-(4-methyl-5-phenyl-1,2,3-triazol-2-yl)-benzofurane-2-carboxylic acid obtained as an intermediate product in a yield of 87% of theory has a melting point of 245°–248° C. The acid chloride prepared therefrom in 90% yield melts, after recrystallisation from cyclohexane, at 159°–160° C.

EXAMPLE 4

3.0 g of the compound of the formula (301) are dissolved in 150 ml of chlorobenzene by heating under reflux. 2.0 ml of dimethyl sulphate are added dropwise to the solution at 100° C. When the dropwise addition has ended, the mixture is stirred under reflux for 4 hours. During this period, the quaternary salt precipitates. The mixture is allowed to cool to 90° and the precipitate is filtered off, rinsed several times with hot chlorobenzene and dried at 100° C. under an oil pump vacuum. 3.6 g (92% of theory) of the compound of the formula

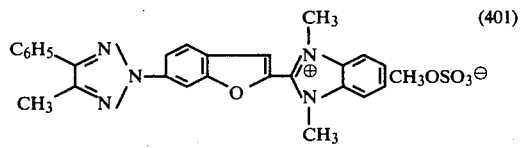

are obtained in the form of yellow crystals. The compound dissolves in water to give a solution which exhibits a neutral blue fluorescence in daylight.

The compound is outstandingly suitable for brightening polyacrylonitrile fibres.

If, instead of the compound of formula (301), the same amounts of the compounds of the formulae (302) or (303) or (304) are used and the procedure followed is otherwise as described above, the quaternary salts of the following formulae are obtained

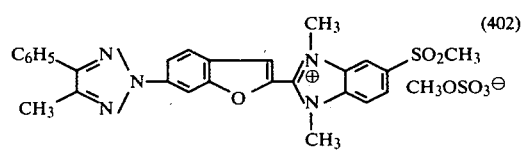

or

-continued

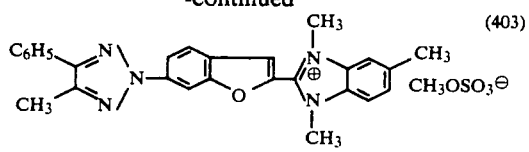

or

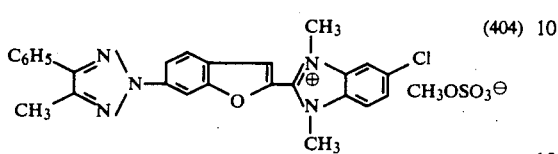

These products have similar properties to the compound (401) described above.

EXAMPLE 5

If, instead of 6.8 g of 6-(4-methyl-5-phenyl-1,2,3-triazol-2-yl)-benzofurane-2-carboxylic acid chloride, the equivalent amount of 6-(4-phenyl-1,2,3-triazol-2-yl)-benzofurane-2-carboxylic acid chloride is used and the procedure followed is otherwise as described in Example 3, the benzimidazole of the formula

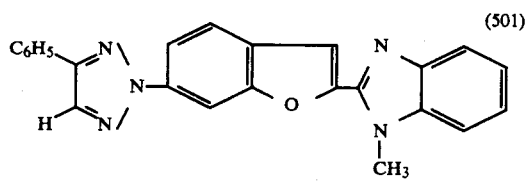

is obtained, in 65% yield, in the form of yellowish crystals which exhibit a red-violet fluorescence in solution.

The compounds of the formula

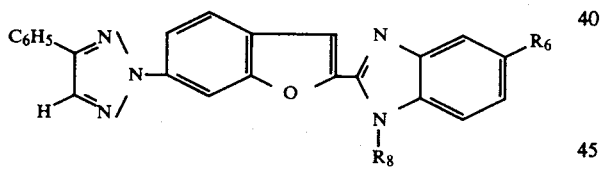

listed in Table 1 are obtained in an analogous manner.

TABLE 1

| Compound | $R_8$ | $R_6$ | Color of fluorescence in solution |
|---|---|---|---|
| 502 | $CH_3$ | $CH_3$ | red-violet |
| 503 | $CH_3$ | Cl | blue-violet |
| 504 | $CH_3$ | $SO_2$—$CH_3$ | blue-violet |
| 505 | H | H | red-violet |
| 506 | H | $CH_3$ | red-violet |
| 507 | $CH_2$—$C_6H_5$ | H | red-violet |
| 508 | $CH_2$—$C_6H_5$ | $CH_3$ | red-violet |

The 6-(4-phenyl-1,2,3-triazol-2-yl)-benzofurane-2-carboxylic acid chloride used as the starting material is obtained by a preparation analogous to the preparation, described in Example 1, of 6-(naphth[1,2-d]-1,2,3-triazol-2-yl)-benzofurane-2-carboxylic acid chloride when 4-(naphth[1,2-d]-1,2,3-triazol-2-yl)-salicylaldehyde is replaced by 4-(4-phenyl-1,2,3-triazol-2-yl)-salicylaldehyde and the procedure followed is otherwise as described in that example.

The 6-(4-phenyl-1,2,3-triazol-2-yl)-benzofurane-2-carboxylic acid obtained as an intermediate product in a yield of 80% of theory melts at 195°–199° C. The acid chloride prepared therefrom in 85% yield melts, after recrystallisation from toluene, at 288°–229° C.

EXAMPLE 6

To prepare the quaternary salts of the formula

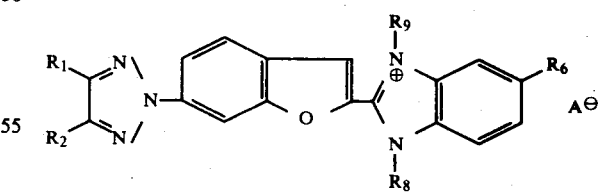

listed in Table 2, the procedure followed is analogous to that described in Example 4.

TABLE 2

| Compound | $R_8$ | $R_6$ | Colour of fluorescence in solution |
|---|---|---|---|
| 601 | $CH_3$ | H | blue-violet |
| 602 | $CH_3$ | $CH_3$ | blue-violet |
| 603 | $CH_3$ | Cl | blue |
| 604 | $CH_3$ | $SO_2$—$CH_3$ | neutral blue |
| 607 | $CH_2$—$C_6H_5$ | H | blue-violet |
| 608 | $CH_2$—$C_6H_5$ | $CH_3$ | blue-violet |

EXAMPLE 7

The compounds of the formula listed in Table 3 and the quaternary compounds of the formula are obtained in an analogous manner to that described in the above examples.

TABLE 3

| Compound | $R_1$ | $R_2$ | $R_6$ | $R_8$ | $R_9$ | $A^⊖$ | Colour of fluorescence in solution |
|---|---|---|---|---|---|---|---|
| 701 | $C_2H_5$ | $CH_3$ | H | H | — | — | red-violet |
| 702 | $C_2H_5$ | $CH_3$ | H | $CH_3$ | — | — | red-violet |
| 703 | $C_2H_5$ | $CH_3$ | H | $CH_2$—$C_6H_5$ | — | — | red-violet |
| 704 | $C_2H_5$ | $CH_3$ | $CH_3$ | H | — | — | red-violet |
| 705 | $C_2H_5$ | $CH_3$ | $CH_3$ | $CH_3$ | — | — | red-violet |

TABLE 3-continued

| Compound | $R_1$ | $R_2$ | $R_6$ | $R_8$ | $R_9$ | $A^\ominus$ | Colour of fluorescence in solution |
|---|---|---|---|---|---|---|---|
| 706 | $C_2H_5$ | $CH_3$ | Cl | H | — | — | blue-violet |
| 707 | $C_2H_5$ | $CH_3$ | Cl | $CH_3$ | — | — | blue-violet |
| 708 | $C_2H_5$ | $CH_3$ | $SO_2$—$CH_3$ | $CH_3$ | — | — | blue |
| 712 | $C_2H_5$ | $CH_3$ | H | $CH_3$ | $CH_3$ | $CH_3OSO_3^\ominus$ | red-violet |
| 713 | $C_2H_5$ | $CH_3$ | H | $CH_2$—$C_6H_5$ | $CH_3$ | $CH_3OSO_3^\ominus$ | red-violet |
| 715 | $C_2H_5$ | $CH_3$ | $CH_3$ | $CH_3$ | $CH_3$ | $CH_3OSO_3^\ominus$ | blue-violet |
| 717 | $C_2H_5$ | $CH_3$ | Cl | $CH_3$ | $CH_3$ | $CH_3OSO_3^\ominus$ | blue |
| 718 | $C_2H_5$ | $CH_3$ | $SO_2$—$CH_3$ | $CH_3$ | $CH_3$ | $CH_3OSO_3^\ominus$ | blue |
| 721 | (furan) | | H | H | — | — | blue-violet |
| 722 | (furan) | | H | $CH_3$ | — | — | blue-violet |
| 723 | (furan) | | $CH_3$ | $CH_3$ | — | — | blue-violet |
| 724 | (furan) | | $SO_2CH_3$ | $CH_3$ | — | — | blue |
| 725 | $CH_3$ | $OCH_3$ (furan) | H | H | — | — | blue |
| 726 | " | | H | $CH_3$ | — | — | blue |
| 727 | " | | $CH_3$ | $CH_3$ | — | — | blue |
| 728 | " | | $SO_2CH_3$ | $CH_3$ | — | — | neutral blue |
| 729 | " | | Cl | $CH_3$ | — | — | neutral blue |
| 730 | $CH_3$ | $OC_4H_9$-n (furan) | H | H | — | — | blue |
| 731 | " | | H | $CH_3$ | — | — | blue |
| 741 | (furan) | | H | $CH_3$ | $CH_3$ | $CH_3OSO_3^\ominus$ | blue |
| 742 | " | | $CH_3$ | $CH_3$ | $CH_3$ | $CH_3OSO_3^\ominus$ | blue |
| 743 | " | | $SO_2CH_3$ | $CH_3$ | $CH_3$ | $CH_3OSO_3^\ominus$ | neutral blue |
| 744 | $CH_3$ | $OCH_3$ (furan) | H | $CH_3$ | $CH_3$ | $CH_3OSO_3^\ominus$ | blue |
| 745 | " | | $CH_3$ | $CH_3$ | $CH_3$ | $CH_3OSO_3^\ominus$ | blue |
| 746 | $CH_3$ | $OC_4H_9$-n (furan) | H | $CH_3$ | $CH_3$ | $CH_3OSO_3^\ominus$ | blue |

The quaternary salts listed above dissolve in water giving solutions which exhibit a blue to blue-green fluorescence in daylight.

EXAMPLE 8

Polyacrylonitrile textile fabrics are treated at the boil for 30 minutes, in a liquor ratio of 1:40, with a dye liquor which contains 0.2% of the compound of the formula (401), 8% of 50% strength Na chlorite, 4% of Na nitrate and 4% of chlorite stabiliser (all the percentage data are relative to the textile material) and which is adjusted to pH 3.5 with formic acid. After rinsing and drying the fabric, a polyacrylonitrile fabric which has been brightened very well and brilliantly is obtained.

Similar results are obtained when the procedure followed is the same as described above but the compounds of the formulae (201), (402), (403), (404), (601), (602), (712), (715) or (718) are employed.

We claim:
1. A compound of the formula

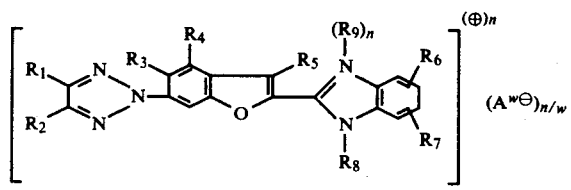

in which
$R_1$ is alkyl with 1 to 12 carbon atoms, alkoxy with 1–4 carbon atoms, benzyl, styryl, or phenyl optionally be substituted by alkyl with 1–4 C atoms, phenyl, alkoxy with 1–4 C atoms or chlorine,
$R_2$ is hydrogen cyano, carboxyl, $C_1$-$C_4$-alkylcarbonylamino, benzoylamino or $R_1$, or
$R_1$ and $R_2$ together are a fused naphthalene ring or benzene ring optionally substituted by alkyl with 1 to 4 carbon atoms and/or alkoxy with 1 to 4 carbon atoms, $R_3$ and $R_4$ each independently is hydrogen, methyl, ethyl, methoxy or chlorine, $R_5$ is hydrogen, alkyl with 1 to 4 carbon atoms, or phenyl optionally substituted by methyl and/or methoxy, $R_6$ is hydrogen, alkyl with 1 to 4 carbon atoms, methoxy, chlorine, alkylsulphonyl with 1 to 4 carbon atoms, cyano, sulpho or carboxyl, $R_7$ is hydrogen, methyl, methoxy or Cl, $R_8$ is alkyl with 1 to 4 carbon atoms, hydroxyalkyl with 2 to 4 carbon atoms, cyanoethyl, or phenyl, cyclohexyl of benzyl optionally substituted by chlorine, methyl or methoxy, $R_9$ is alkyl with 1 to 4 carbon atoms optionally substituted by hydroxyl or alkoxy with 1 to 4 carbon atoms, benzyl optionally substituted by chlorine or methoxy, or $-CH_2CN$, $-CH_2CONH_2$ or $-CH_2COOR$, R is alkyl with 1 to 4 carbon atoms, n is 0 or 1, $A^\ominus$ is a colorless anion of an organic or inorganic acid, and w is the valence of A.

2. A compound according to claim 1, in which $A^-$ is a halide, formate, acetate, lactate, $CH_3SO_4^\ominus$, $C_2H_5SO_4^\ominus$, $C_6H_5SO_3^\ominus$, p—$CH_3$—$C_6H_4SO_3^\ominus$, p—Cl—$C_6H_4SO_3^\ominus$, carbonate or bicarbonate.

3. A compound according to claim 1, in which $R_3$, $R_4$, R and $R_7$ each is hydrogen, and $A^-$ is halide, $CH_3SO_4^-$, $C_2H_5SO_4^-$ or p—$CH_3$—$C_6H_4SO_3^-$.

* * * * *